United States Patent [19]

Tundo

[11] Patent Number: 4,632,742
[45] Date of Patent: Dec. 30, 1986

[54] PROCESS FOR THE DECOMPOSITION AND DECONTAMINATION OF ORGANIC SUBSTANCES AND HALOGENATED TOXIC MATERIALS

[75] Inventor: Pietro Tundo, Turin, Italy

[73] Assignee: Sea Marconi Technologies S.p.A., Turin, Italy

[21] Appl. No.: 711,404

[22] Filed: Mar. 13, 1985

Related U.S. Application Data

[63] Continuation-in-part of Ser. No. 517,781, Jul. 27, 1983, abandoned.

[30] Foreign Application Priority Data

Mar. 10, 1983 [IT] Italy .............................. 19992 A/83

[51] Int. Cl.$^4$ ..................... B01J 19/08; B01J 19/10; B01J 19/12
[52] U.S. Cl. ............................. 204/158.21; 210/909
[58] Field of Search .................. 210/748, 909; 204/158 P, 158 S, 165, 158.21

[56] References Cited

U.S. PATENT DOCUMENTS

| | | | |
|---|---|---|---|
| 4,144,152 | 3/1979 | Kitchens | 204/158 R |
| 4,246,255 | 1/1981 | Grantham | 208/262 |
| 4,297,186 | 10/1981 | Killer | 204/165 |
| 4,410,422 | 10/1983 | Brunelle | 208/262 |
| 4,447,541 | 5/1984 | Peterson | 435/264 |

FOREIGN PATENT DOCUMENTS 2814126 10/1979 Fed. Rep. of Germany ... 204/158 P

*Primary Examiner*—Howard S. Williams
*Attorney, Agent, or Firm*—Bucknam and Archer

[57] ABSTRACT

A method for the decomposition of an halogenated organic compound is described which comprises reacting the compound with a reagent which consists of (a) at least one member which is a polyethyleneglycol, Nixolen ®, an alcohol or a polyhydroxy compound, (b) a base, and (c) an oxidizing agent or a source of radicals, in the absence of oxygen. The method is applicable to the decontamination of mineral oils and soil contaminated with polychlorobiphenyls, polychlorodibenzofurans, polychlorodibenzodioxins, DDT and other halogenated organic compounds.

The different possible formulations of such reagents allow the preparation of stable reactive mixture, which can be either liquid or solid; the liquid reagents are particularly suitable for the decontamination of porous surfaces such as cement, sandstone, asphalt and for the decontamination of parts of plants contaminated by PCBs.

The use of microwaves during the decontamination process proved to be particularly advantageous.

14 Claims, 4 Drawing Figures

GAS-CHROMATOGRAM N° 2 (EXAMPLE 1)
OIL AFTER TREATMENT (CONC. 1 X 10$^{-3}$)

GAS-CHROMATOGRAM N° 2 (EXAMPLE 1)
OIL AFTER TREATMENT (CONC. 1 X 10$^{-3}$)

GAS-CHROMATOGRAM N° 3 (EXAMPLE 5)
ENVIRONMENTAL DECONTAMINATION: BLANK AFTER 7 DAYS

GAS-CHROMATOGRAM N°4 (EXAMPLE 5)
ENVIRONMENTAL DECONTAMINATION: METHOD A AFTER 7 DAYS

PROCESS FOR THE DECOMPOSITION AND DECONTAMINATION OF ORGANIC SUBSTANCES AND HALOGENATED TOXIC MATERIALS

This application is a continuation-in-part of application Ser. No. 06/517,781, filed July 27, 1983, now abandoned.

The present invention relates to the chemical decomposition of organic compounds, and more specifically polyhalogenated organic compounds. Still more specifically, the present invention relates to a novel method for the chemical decomposition of polyhalogenated organic compounds which is carried out at low temperature and for short periods of time and, therefore, may be used conveniently also for the decontamination of soil and surfaces which contain pollutants, for instance tetrachlorodibenzoparadioxin (dioxin), polychlorobiphenyls, DDT, Kepone, etc. and brominated and fluorinated analogs.

It is well know that polyhalogenated organic compounds are a source of ecological problems due to the great stability of the carbon-chlorine bond and the resulting chemical inactivity, so that they have a tendency to accumulate in the environment, thus causing a number of toxic effects which extend from the ecology of the environment, that is the soil, the air, the vegetation, water and animals, to humans. Several scientific articles have been published in the last few years on the analytical and toxicological aspects of dioxins and polychlorobiphenyls. In spite of the fact that several laws have been introduced which are always more restrictive in an effort of controlling and limiting the problem, there are still many industrial applications of the polyhalogenated organic compounds, and in particular polychlorobiphenyls (PCB), which are being used as insulating oils for transformers and condensers, lubricating oils and heat conductors as well as additives in the production of paper, glues, paint, asphalt, synthetic fibers, plastic materials, insulating coatings, etc.

In addition, a very high percentage of contamination due to PCB has been found also in machinery such as transformers and condensers in which the PCB are substituted by mineral oils: this high percentage of contamination varies between 38% (Reference: 40 CFR Part 761 of May 31, 1979 EPA-USA) and 41% of the existing installations (according to SEA-Marconi in Italy) and is caused by errors of manipulation, inappropriate connections and reconversion and utilization of contaminated installations.

The dangers connected with the use of PCB are further increased due to their transformation into substances which are still more toxic such as the polychlorodibenzofurans (PCDF) and polychlorodibenzodioxins (TCDD and HCDD, which are respectively tetrachloro- and hexachloro-dibenzodioxins) at the high temperature resulting from occurrences such as explosions or fires.

It is, therefore, clear the usefulness of a method of chemical degradation capable of being carried out in open systems and in the absence of drastic conditions which, by breaking the bond between carbon and chlorine could obviate the lack of biodegradability typical of polyhalogenated compounds.

Further, a method of chemical decomposition is clearly preferable to other methods for the decontamination such as burning, washing or adsorption, which methods in addition to being less effective, causing several environmental problems.

The methods used in the present state of the art do not solve the problem in all of its aspects. For instance, U.S. Pat. No. 4,337,368 describes a method in which the organic halogenated compounds are decomposed by treatment with an alkali metal and a polyethyleneglycol in the presence of oxygen and high temperature. The method is not continuous because it requires, first of all, the formation of the reagent and in a successive stage, the decomposition of the organic compound. The main drawbacks of this procedure consist of the high temperature required for the reaction of decomposition and the necessity of using metallic sodium which, as it is well known, is dangerous and inconvenient.

European Patent Application No. 60089 and U.S. Pat. No. 4,353,793, describe a method which overcomes the problems of using sodium by replacing sodium with an hydroxide or an alkali metal. However, the method of this patent application requires always two separate stages and the decontamination temperature is high, 90°-145° C. Further, when there are used the two methods described hereinabove for the decontamination of dielectric fluids of transformers, the resulting decontaminated fluid, due to the high temperatures, presents different characteristics so that it is necessary to require further treatment of the fluid prior to its reuse.

The two procedures described hereinabove finally cannot be utilized for the decontamination of wide surface areas, walls, soils, etc., due to the practical impossibility of maintaining in situ high temperatures for a long period of time and for the decontamination of dioxins TCDD and HCDD or polychlorodibenzofurans.

The object of the present invention is to overcome the drawbacks of the methods known in the art. More specifically, the present invention provides a method according to which the polyhalogenated organic compounds are placed in contact with a reactive mixture which comprises an alkali or alkaline earth metal carbonate or bicarbonate, a polyethyleneglycol, Nixolens ®, an alcohol or polyhydroxy compound and a source of free radicals such as a peroxide, a persalt, or a metal of high valence state or another compound which by heating becomes a source of radicals, for instance azoisobutyronitrile and organic peroxides in general.

The terms polyethyleneglycol (PEG) and alcohols are used herein to designate compounds having the general formula

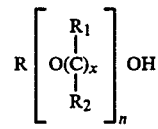

wherein:

$x \geq 2$;

n is zero or an integer from 2 to 400;

R is a linear or branched $C_1$–$C_4$ alkyl when n=0; or is hydrogen, linear or branched $C_1$–$C_{20}$ alkyl, aryl, aralkyl or acyl when n=2–400;

$R_1$ and $R_2$, which may be the same or different, are hydrogen, linear or branched $C_1$–$C_4$ alkyl, $C_5$–$C_8$ optionally substituted cycloalky, optionally substituted aryl.

In said formula, when n is different from zero, x is generally 2.

In this category fall the alcohols having low molecular weight, polyethyleneglycols and polyethyleneglycols which contain one ether or one ester group, the Tritons ® which are monoisooctylphenylesters of polyethyleneglycols, and Tweens ® which are polyoxyethylene sorbitan mono-oleates, pentaerythritol and its derivatives. In particular, the polyethyleneglycols are compounds of formula H(OCH$_2$CH$_2$)$_n$OH; depending on the value of n, these compounds are liquid or solid. When n is greater than about 20, they are solids of low melting point. Also solids of low melting point are the monoalkylethers of PEG when the alkyl group has sufficiently high molecular weight, such as in C$_{12}$H$_{25}$(OCH$_2$—CH$_2$)$_{12}$OH (Brij ®35): the choice of the molecular weight of the polyethyleneglycols, in accordance with the method of the present invention, is a function of the temperature or the type of decontamination.

For instance, the solid PEGs of low melting point are used for the decontamination of the environment because they are used for providing a solid crust on the surface being decontaminated or are suitable for the decontamination which occurs at a temperature higher than 50° C. On the other hand, for the decontamination which is to be carried out at room temperature which constitutes a particular aspect according to the present invention, one prefers compounds and mixtures which are liquid at room temperature: compounds of formula PEG in which n is less than 20, alcohols and polyhydroxy compounds.

The term polyhydroxy compounds and derivatives is used herein to indicate compounds having the following general formula:

in which n is a number between 100 and 10,000 and R$_3$ is hydrogen or a linear or branched C$_1$-C$_6$ alkyl.

The Nixolens ®, lubricant oils having low toxicity and widely used in the industry, are condensation products between ethylene oxide and propylene oxide; because of their random condensation, it is not possible to give a simple general formula for them. The ethylene and propylene % in the polycondensation reaction is responsible for the chemical and physical properties of the final product. Three types are commercially known: Nixolens ®NS: they are compounds having low water solubility and soluble in aliphatic hydrocarbons because of the high percentage of propylene monomers contained therein.

Nixolens ®VS: soluble in water in all proportions and insoluble in aliphatic hydrocarbons, they contain a low percentage of propylene monomers. Nixolen ®SL: they have chemical and physical characteristics which are intermediate between Nixolens ®NS and VS. The different possible kinds of Nixolens ® are also commercially marked by a number following the letters; it refers to the product viscosity which is related to the polymer $\overline{MW}$ (medium molecular weight). Nixolens ® are the preferred reagents for the reaction of the invention because of their physical status and chemical activity: they can be used alone or mixed with high molecular weight PEG, changing thereby the viscosity of the reactive mixture without modifying its chemical activity.

The Nixolens ®VS are the most active while the NS type are the less active. When Nixolens ® are used, the basic compound can be chosen also between the alkali or alkali-earth metal alcoxides and, in this case, the reagent can be formulated also without the oxidizing agent.

Among the basic compounds needed to carry out the dehalogenation reaction, surprisingly, particularly suitable are weakly alkaline compounds, such as the carbonates or bicarbonates of sodium, potassium, lithium, calcium, magnesium or barium. Particularly preferred is sodium bicarbonate because of its low cost. These salts go into solution with time and under stirring in the liquid mixture of the reagents. However, it is not necessary to achieve complete solubilization of the base because the addition of all the reactants, the base, PEG or polyhydroxy compounds and the radical source, simultaneously or in sequence, without any preestablished order, gives rise to the reaction of dehalogenation in an efficient manner at an essentially equal rate.

The degree of basicity of the solution does not appear to be decisive for the purpose of the reaction: the presence of water up to 35% of the reactive mass, although it decreases the anionic activation exerted by the agents (PEGs, Nixolens) which form a complex with the organic cation, does not influence to a substantial extent the rate of the reaction.

As a source of free radicals, there may be used conveniently the peroxides and superoxides of alkali metals and alkaline earth metals, persalts such as persulfates and perborates of alkaline earth metals, and ammonium in the anhydrous or hydrate form, salts of metals in a high valence state such as lead tetraacetate, sources of free radicals such as the alkyl peroxides and hydroperoxides, acyl peroxides, azoisobutyronitrile and, in general, every other oxidizing agent or an agent which is a source of free radicals. Na$_2$O$_2$ and BaO$_2$ are particulary preferred.

The presence of oxygen, therefore, it is not necessary and this may be advantageous in the case of decontamination of industrial mineral oils, which particularly at high temperatures are easily inflammable.

The decontamination reaction of the industrial oils may be carried out in accordance with the present invention in a closed container out of the contact with air and also under vacuum. It has been found that only the use of sodium peroxide requires some precautions particularly to avoid the formation of sparks which may be formed during the course of the reaction (sparks of this type have been observed also according to the methods described in the prior art). These precautions, in any event, are required exclusively when PEG of low molecular weight is used, such as the mono-, di-, tri-, tetra- and pentaethyleneglycols, for the reactions which are carried out in the presence of Na$_2$O$_2$ at a temperature above 50° C.

A further advantage of the reagent according to the present invention, resides in its stability even in air which permits the storage for an indefinite period of time with the only precaution of avoiding an excessive adsorption of water, due to hygroscopicity. Further, it is not necessary, in direct contrast with the methods of the prior art, to prepare the reagents previously but the process may be carried out continuously and takes place in a single step.

According to a preferred embodiment of the present invention, the viscosity, adhesiveness and compactness can be easily modified by changing the Nixolens ® type (even by using mixtures of different Nixolens ®, or their mixture with high M.W.), the base amount (generally ranging from 5 to 40% b.w.) and on the peroxide amount (usually ranging from 0.1 to 10% b.w.).

Instead of PEG, in order to further decrease the Nixolens ® viscosity, organic solvents such as monoalkyl low M.W. glycols (usually monomethyl and monobutyl ethers of diethylene glycol), dioxane, glyme, diglyme, xilenes, ecc., can also be used.

They are suitable for a specific and not general application because they do not increase the reaction rate but sometimes they decrease it; for this reasons, if a product having an intermediate viscosity is desired, and starting from PEG, it is preferable adding the latter with low viscosity Nixolens ® rather than with said organic solvents.

The reagent according to the invention decomposes halogenated organic compounds, thus producing the corresponding halides of an alkali or an alkaline earth metal. It has been found by studying the percentage of chlorine in the halogenated compounds and the quantity of NaCl produced during the reaction, that the reaction leads to the complete removal of all the atoms of chlorine in the pollutant. For this reason, the stoichiometry of the reagents must depend on the percentage of chlorine in the substance to be decomposed: the molar ratio must be, therefore, base/Cl greater than or equal to 1 and oxidizing agent/Cl greater than or equal to 0.5.

It is very surprising that in accordance with the method of the present invention, it is not absolutely necessary to use high reaction temperatures, in spite of the fact that are used bases which are much weaker than the bases used in the method according to the prior art. The fact that the dehalogenation may be carried out at room temperature leads to many substantial advantages. For instance, it is possible to carry out the decontamination of the environment on a large scale, and in the case of the decontamination of great quantities of industrial oils, it is possible to operate under conditions of increased safety, substantial saving the energy and simplification and acceleration of the material being consumed. In addition, in direct contrast with the methods known in the art, the oil being decontaminated in accordance with the process of the present invention, offers superior functional and dielectric properties because in addition to the destruction of the halogenated compounds, a series of accompanying effects is noted such as the abolition of particles in suspension, the dehumidification, the deacidification and the decolorization of the oil itself, which when it is treated by the methods known in the art, would, on the other hand, present a substantial blackening due to side reactions, the high temperatures, with obvious difficulties in the immediate recycling.

The process according to the present invention, in addition to being economical and safe, is also rapid because a period of a few hours is sufficient for an almost total decontamination, greater than 99%.

The reaction is more rapid the greater is the degree of halogenation and, therefore, the toxicity and the non-biodegradability of the organic compound to be destroyed. Also the pollutants of soil or surfaces may be adequately treated in accordance with the method of the invention, including the contamination caused by dioxins and PCDF, the polyhalogenated compounds which are the most stable and most toxic.

Dioxins and the PCDF compounds are formed by reactions at high temperature between oxygen and other halogenated compounds, such as trichlorophenols and PCB, which reactions occur after an accident such as the well-known accident in Seveso, Italy and the blowing-up of a transformer of a building in the United States, as well as the incinerators of refuse material or after the combustion of wood which is impregnated with trichlorophenol and other antifungal polychlorinated agents.

The method of the present invention permits a rapid and complete decontamination caused by dioxins and PCDF using inexpensive reagents operating at room temperature also in situ, such as, for instance, on soils which are not particularly dry and without their removal.

The reagent can also be fitted, by changing the viscosity for the decontamination of both porous (cement, sandstone, asphalt) and smooth (glass, metal, etc.) polluted surfaces.

For non porous surfaces a reagent will be preferably used which is solid or able to form a solid film so as to protect the environment from the pollutant and which can be removed after the decontamination (mechanically or by ultrasounds) leaving a decontaminated surface and a no-longer toxic residue. In case of porous surfaces, a liquid reagent, able to penetrate into the polluted material, will be preferred.

A decontamination reagent with low viscosity is also necessary to decontaminate parts of a plant and for their functional recovery (for instance, parts of an electric transformer). In this case it is easier to dip the part in the reagent and leave it until complete decontamination.

It is evident that the reagent, here used in excess, will be used again several times till exhaustion; it can be recycled by adding the active components, by removing polymers, inorganic salts and incrustations deposited during operation.

In order to promote the decontamination process, it is advisable to remove at the start of the operation, possible incrustations present on the surfaces, even when the surfaces of a plant's part are concerned; it proved to be convenient to carry out this operation by putting the reagent containing the contaminated part in an ultrasounds bath which is operated at the start of the operation. The stirring of the reagent inside the bath can be obtained by using either a recycle pump or a mechanical stirrer.

The decontamination process is made more effective if, during the reaction, the reagent is sometimes stirred and heated in order to make easier the diffusion of the different components. With this aim, the use of an infrared wavelength laser proved to be advantagenous, specially for the applications on non porous surfaces.

Even more advantagenous as an application method turned out to be the use of microwaves, for all the operation steps, that is for the reagents formulation, for the preparation of the polluted material to be treated and for the decontamination reaction itself. It has been in fact noticed that a more homogeneous heating of the reagent mixture is obtained if the latter is subjected to microwaves.

Moreover, the preventive microwave treatment of surfaces of cement, sandstone, soil and parts of plants, even for a very short period (from few seconds to few minutes) causes an high drying of the material; this is not only advantagenous because the amount of water is reduced, but above all because the material's pores and interstices are freed and are therefore more accessible to the reagent penetration.

Surprising results have been moreover obtained by microwave irradiation of the reaction mixture: comparing similar reaction conditions (temperature, reagent composition and amounts of present PCBs), it has been shown that the reaction rate in the presence of (Example 8) microwaves is at least 10 times higher than that obtained in their absence. Similar results have been obtained for the decontamination of porous surfaces where the microwaves method has the more evident advantages: they penetrate into the material without directly affecting the solid material. The dehalogenation reaction is thus selectively promoted and contemporaneously, with a substantial energy and time saving (it is not necessary to stress the decisive importance of said parameters from the economic point of view), the heating, diffusione and stirring of the reagents in those internal zones where it would be difficult to act otherwise.

When soils are considered it has also been found that the process according to the present invention may be rendered more efficient by operating in the presence of an electric field obtained by application of electrodes on the surfaces or in the soil to be decontaminated. In this manner, the soil is dehumidified and drained of hydrosoluble components and the dehalogenation occurs more easily, probably also because the free radical reaction and the phenomena of transportation of the reagents occur more easily due to the action of the electric field.

The reagent application can be carried out by spraying (liquid reagents), spreading, brushwork, rolling or other suitable method.

During the reaction, organic free radicals are produced which, if the temperature is high enough ($>70°$ C.), can react with the PEGs and Nixolens® molecules; it has been in fact verified that, even in the absence of halogenated compounds, the heating of the prepared reagent, produces a slow evolution of $H_2$, CO, $CH_4$, ethylene etc.

The preparation of the dehalogenating reagent must not be carried out on large scale operating at high temperatures without suitable safety measures, because explosions could result; the reagent preparation can be easily and conveniently carried out at temperatures lower than 70° C., and preferably at room temperature, where the production of said gases is minimum or quite inexistent.

Also under this aspect, it is particularly advantageous the use of Nixolens® which are liquid even at low temperatures (for instance up to about $-20°$ C.) and are therefore able to rapidly dissolve the other solid components necessary for the preparation of the final formulation. It is also clear that this rule, deriving from safety reasons, must not contrast with the chemical activity of the prepared reagents. The use of liquid Nixolens is useful when alcoxides are used.

The method according to the present invention is therefore particularly flexible because it can be indifferently carried out in the absence of presence of air, oxygen, water and stirring and in a wide temperature range. The reagent is moreover easily prepared, it is not influenced by the type of the halogenated compound to be destroyed and yields practically non toxic compounds in comparison with the starting pollutants and such as to easily undergo a further biodegradation.

The detoxifying activity of the reagent has been studied by orally administering to guinea-pigs doses of the 2,3,7,8 TCDD and reagent reaction mixture—suitable neutralized—at different times. From the histopathological analysis of target organs such as liver, spleen and thymus and from the body weight increase in comparison with control groups treated with the reagent along or with 50% ethanol, a total lack of toxicity was evidenced for doses of mixtures equivalent to 431 $\mu g/kg$ of dioxin initially present, after 1 h and 45 min. at 85° C., and to 660 of $\mu g/kg$ of dioxin initially present, after 5 h at 85° C., with a remarkably effective detoxification, considering that the $LD_{50}$ reported for TCDD before the decomposition is about 1 $\mu g/kg$.

In the examples which are reported hereinbelow, which illustrate further the present invention and the results which may be obtained, the reaction mixture is utilized to achieve the destruction of the contaminant in three different manners:

1. The contaminant is added as such to the reaction mixture and the latter is left standing, with or without stirring, at a predetermined temperature;

2. The contaminant is added in solution of a solvent which may be either miscible, such as toluene, or immiscible in the reactive phase, such as n-hexane.

In the latter case, the two phases are stirred. An application of this method is the decontamination of oils and dielectric fluids (new, used and exhausted), mineral, silicone and others used, for instance, in trasformers operating at high, medium and low tension as rectifiers, rheostats, electric power switches or diathermic fluids, hydraulic fluids, etc.

The stirring in this case, while carrying out the reaction in a five-liter reactor, is guaranteed by ultrasonic energy which is more efficient than simple mechanical stirring. As it is shown by the $^1$H-NMR spectra of the oils treated according to the procedure, the PEG or Nixolen remains dissolved in the oil to a very small extent (less than 1%), almost undetectable. This low amount does not change the dielectric properties of the fluid which may be reused immediately without any further treatment according to the normal applications of the fluid. After analyzing the properties and the dielectric characteristics of the oils, it has been found that with respect to the initial oil, they are substantially improved. This improvement has not been found when the reaction is carried out according to the procedure described in Example III of the European Patent Application No. 60089.

3. The reaction mixture, of suitable viscosity, is applied onto a glass surface or a cement surface, an asphalt surface or metallic surfaces which may be painted, the decontaminant, that is the polyhalogenated compound, having first been applied on the surface in a known amount.

The following examples illustrate further the method according to the present invention.

EXAMPLE I

Figure 1:
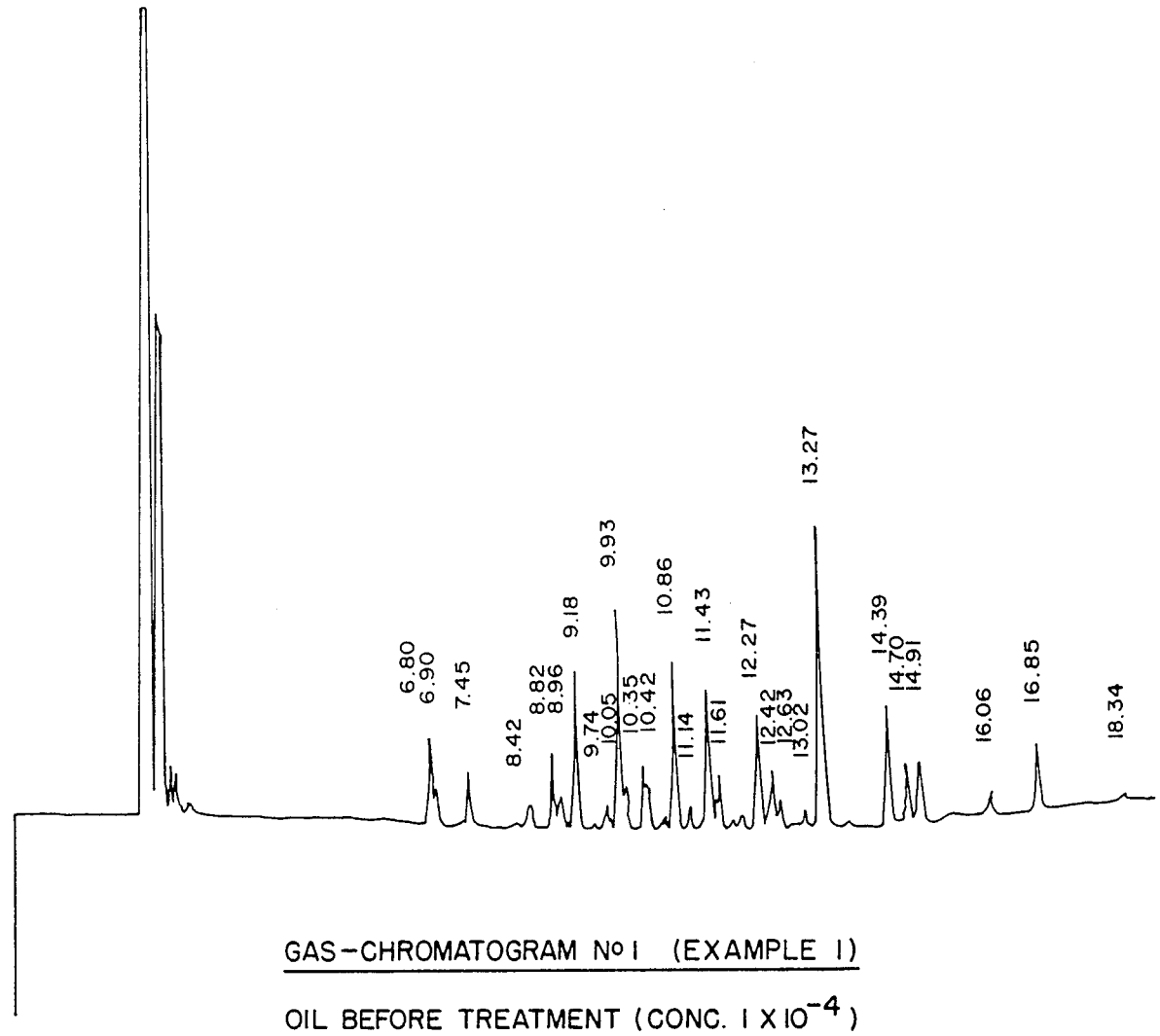
FIG. 1 shows the gas chromatograph of the oil of Example 1 prior to treatment.
Figure 2:
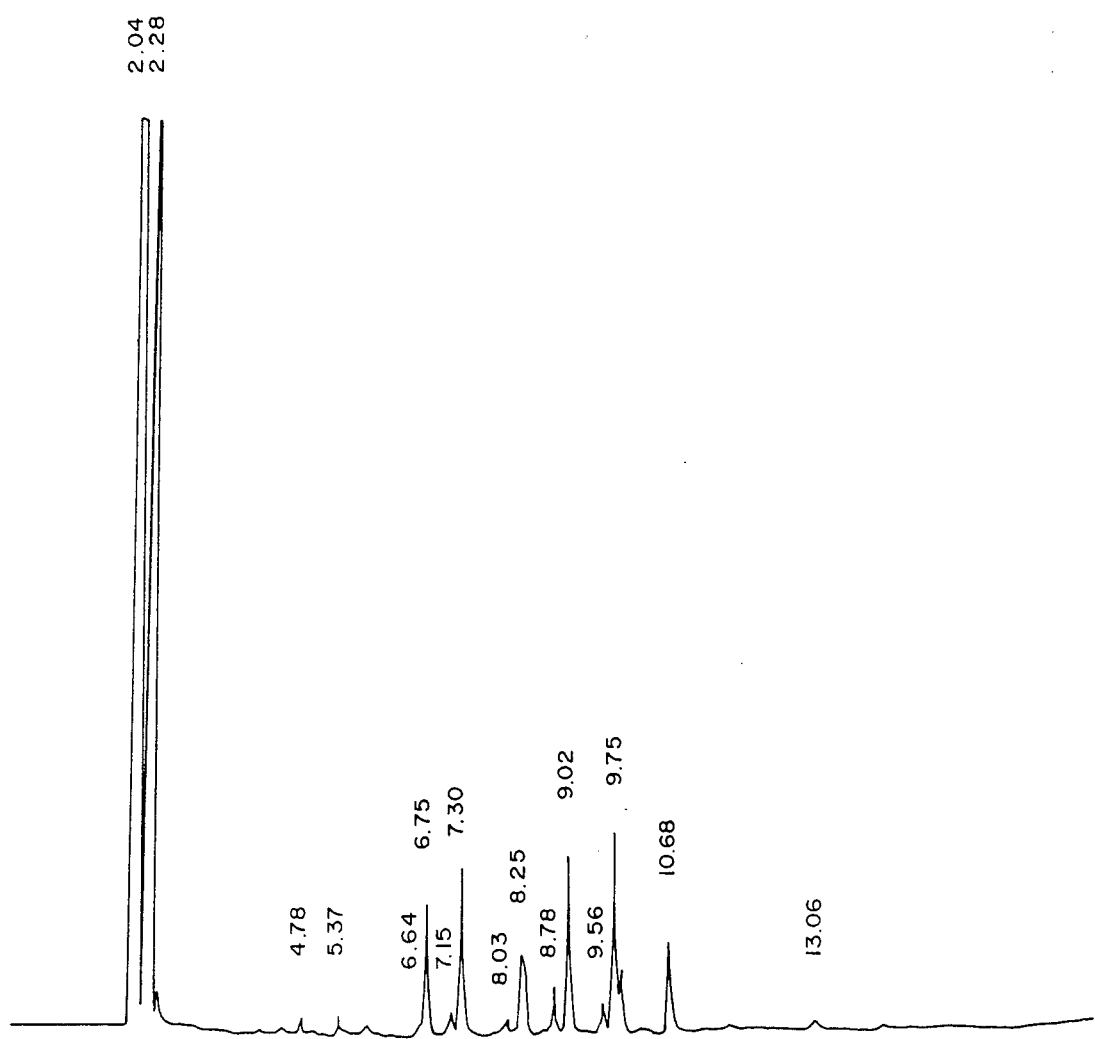
FIG. 2 is the gas chromatogram of the oil of Example 1 after treatment.
Figure 3:
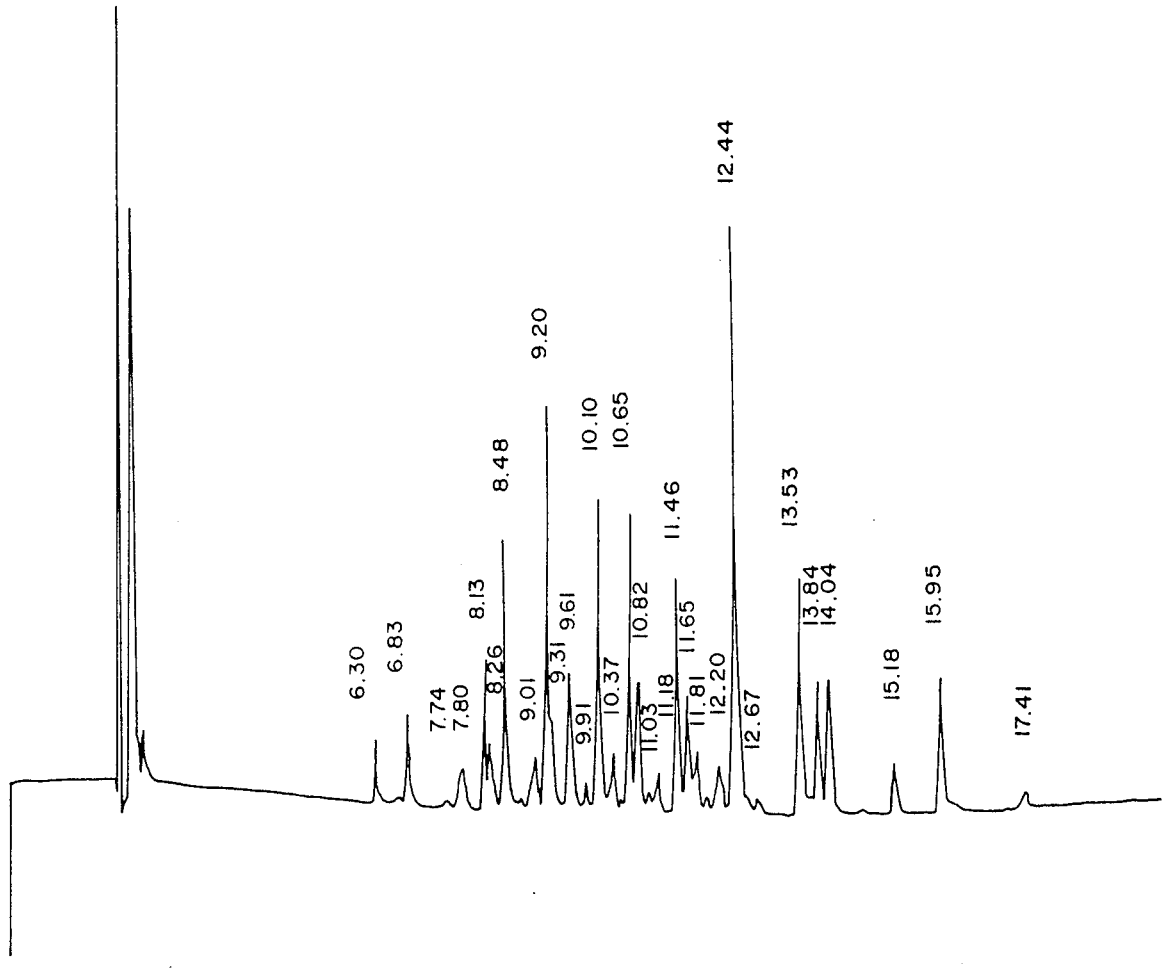
FIG. 3 is the gas chromatogram of Example 5 showing the contamination of the environment prior to application of the method of this application.
Figure 4:
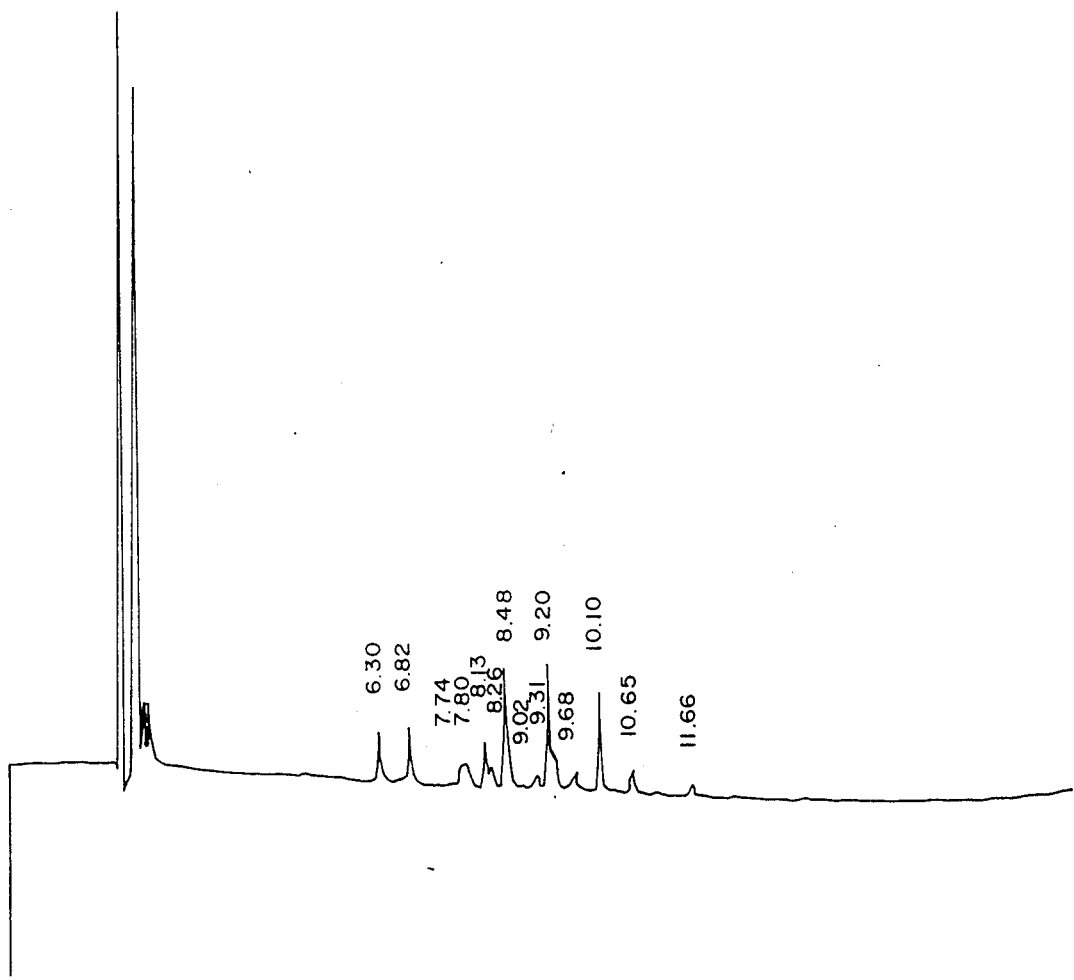
FIG. 4 is the gas chromatogram of the environment after application of the applicant's method.

Decontamination of mineral oil used in high voltage electric power transformers and containing 20,000 parts per million of PCB A sample of mineral oil (Isovoltine ®), 16 cc contaminated with 20,000 parts per million of PCB (in Ascarel, Apirolio 1488 T ®) was placed in a vessel provided with a Teflon ® stopper and warmed at 85° C. by means of a thermostat operating with circulating fluid. Ascarel and Aprilio are dielectric fluids, containing polychlorobiphenyl. Under magnetic stirring, there were added 2.0 g of carbowax 6,000, 0.5 g of base and 0.2 g of oxidizing substance, and finally water. The mixture was kept under stirring for three hours, and after cooling, a portion of the oil which was clear was suitably diluted with n-hexane and analyzed by gas chromatography.

The several reagents being used and the results expressed as parts per million of the residues of PCB in the oil after treatment are reported in Table 1. There are also reported some gas chromatograms of the reaction; gas chromatogram No. 1 refers to the initial oil prior to treatment using gas chromatogram apparatus of Hewlett-Packard HP-5880-A with a capillary column which operates by $^{63}$Ni electron capture.

TABLE 1

| Reagent PEG | Base | Oxidizing Agent | $H_2O$ | Residual PCB in parts per million |
|---|---|---|---|---|
| Carbowax 6000 | $K_2CO_3$ | $Na_2O_2$ | — | 95 |
| Carbowax 6000 | $K_2CO_3$ | $Na_2O_2$ | 0.1 cc | 140 |
| Carbowax 6000 | $K_2CO_3$ | $Na_2O_2$ | 0.3 cc | 1380 |
| Carbowax 6000 | $K_2CO_3$ | $Na_2O_2$ | 0.6 cc | 4350 |
| Carbowax 6000 | $NaHCO_3$ | $Na_2O_2$ | — | 900* |

*Gas chromatogram No. 2

Under the same conditions but using toluene instead of oil in the presence of $K_2CO_3$, the amount of PCB is reduced to 3,100 parts per million. In this case, one obtains a homogeneous solution because toluene solubilizes the reagent.

Under the same conditions, but using n-hexane instead of oil and in the presence of sodium bicarbonate, the content of PCB at the end of the reaction was 700 parts per million.

Under the same conditions, but using a silicone oil in the presence of $K_2CO_3$ (0.2 g), 40 parts per million of residual PCB were detected.

EXAMPLE II

Decontamination of mineral oil used in high voltage electric power transformers containing 1,000 parts per million of PCB with different reagents Under the conditions of Example I, in the presence of $K_2CO_3$ and $Na_2O_2$ at the end of the reaction, there were found 13 parts per million of PCB.

Under the same conditions of Example I and in the presence of $NaHCO_3$ and $Na_2O_2$ at the end of the reaction, there were found 110 parts per million of PCB.

EXAMPLE III

Decontamination of mineral oil which contains 1,000 parts per million of PCB

In a five-liter container were placed 2.4 liters of mineral oil contaminated with 1,000 parts per million of PCB in Ascarel, 200 g of carbowax 1,500, and 30 g of diethyleneglycol monobutylether.

The mixture was warmed to 70° C. and stirred by means of a source of ultrasonic energy (21–50 KHz, Mackston Ultrasonics Ltd.). Potassium carbonate in the amount of 25 g of barium peroxide in the amount of 10 g were then added and stirring and warming were continued for a period of seven hours (Method A). After cooling the reaction mixture, the gas chromatographic analysis of the oil suitably diluted in n-hexane, showed a content of 45 parts per million of PCB.

The necessary analyses were performed on the oil separated by decantation for the purpose of reutilizing it in a high voltage transformer. The reaction described in Example III of European patent application No. 60089 was separately carried out with the same type of contaminated oil using as the reagent, the mixture of PEG having $\overline{PM}$ equal to 400 and aqueous sodium hydroxide (Method B). In the latter case, the oil recovered has a brown-black color. The same analyses which were carried out on this oil, are reported in Table 2.

TABLE 2

| Physical and physico-chemical properties of oils containing PCB after decontamination | | | | | | | | | |
|---|---|---|---|---|---|---|---|---|---|
| | tg factors of electric dispersion* | $H_2O$ parts per million | Acidity mg KOH/g of oil | Appearance and density | Color** | Particles*** | | | |
| | | | | | | >>5 μm | 15 | 50 | 100 |
| Oil prior to the treatment | 0.0232 | 50 | 0.01 | Clear 0.883 | 1.0 | 492 | 44 | 0 | 0 |
| Oil treated according to Method A | 0.0172 | 22 | <0.01 | Clear 0.854 | 1.0 | 260 | 18 | 0 | 0 |
| Oil treated according to Method B | Not determined | 239 | <0.01 | Not carried out | Not measurable (brown) | Not carried out because of excessive torbidity | | | |
| Requirements | 0.2 ÷ 20 | 45 | >0.03 | Must be clear | | | | | |

*IEC 247 (MGB mod. TAMIOO)
**Requirements: ASTM-T 1500 (STANHOPE-SETA Color Comparator ASTM D 1500)
***Particles (HAIAC - Particle Counter PC-420)

On the basis of the results reported hereinabove, it is clear that the method according to the present invention, and specifically Method A, in addition to eliminating PCB from the oil, improves the dielectric properties: the same oil may be used without further treatment as an insulator in transformers.

The same oil, on the other hand, treated according to the comparison method (Method B), does not exhibit these characteristic properties.

Another test was carried out on the same oil according to Method A, but here were added five drops of concentrated sulfuric acid. An oil with the same properties reported in Table 2 (Method A) was obtained, thus showing the optimum effectiveness of the reagent according to the present invention as a neutralizing agent.

EXAMPLE IV

Chemical destruction of TCDD from a hydrocarbon solution

The hydrocarbon n-decane in the amount of 4.0 cc containing four parts per million of 2,3,7,8-TCDD was stirred for two hours at 85° C. in the presence of 1 g of carbowax 6,000, 0.5 g of $K_2CO_3$ and 0.1 g of $Na_2O_2$. The gas-mass analysis showed that there are no phenomena of partition, the dioxin does not pass from the hydrocarbon phase into the PEG phase due to a simple phenomenon of solubility and that the reaction causes the chemical destruction of TCDD with a yield greater than 98%.

The chemical destruction reaction of TCDD occurs also at room temperature. For this purpose, 4 cc of n-hexane containing four parts per billion of TCDD were stirred at room temperature for seven days in the presence of 2.0 cc of tetraethyleneglycol, 0.5 g of $K_2CO_3$ and 0.1 g of $Na_2O_2$, with analogous results.

EXAMPLE V

Decontamination of the environment

On microscopic slides were placed 0.5 µl microliters of n-hexane containing 15,000 parts per million of PCB and the n-hexane was allowed to evaporate.

On other microscopic slides were placed 5.0 µl microliters of n-hexane containing 20,000 parts per million of PCB and the n-hexane was allowed to evaporate.

Decontamination mixtures were prepared by stirring at 85° C. for one-half hour, 4.0 g of Brij 35 R, 2.0 g of potassium carbonate and 0.2 g of sodium peroxide.

There was also prepared molten Brij 35 which was placed on contaminated slides as a control.

The molten mixtures solidified on the slides and then were allowed to stand at room temperature for several days.

After the predetermined periods of time, a slide was placed in a two-phase system consisting of 10 cc of water under conditions providing stirring until the solid mass was dissolved. The organic phase was then analyzed by gas chromatography. In Table 3 are reported results in terms of parts per million of PCB found in the n-hexane solution, which has been analyzed and which refer to the initial solution.

TABLE 3

| Reagent | Part per million of residue after two days | Residual parts per million after seven days |
|---|---|---|
| Control | 15,000 | 15,000* |
| A | 3,900 | 2,500** |

*Gas chromatogram No. 3
**Gas chromatogram No. 4

When iso-octane contaminated with 1,000 parts per million of PCB is used under the same conditions in the presence of $K_2CO_3$ and 0.2 g of sodium peroxide and in the presence of 0.5 g of soil having 10% humidity, at the end of the reaction there is found less than 10 parts per million of PCB.

EXAMPLE 6

Preparation of different reagents and their activity on PCBs

The different types of Nixolens ® used are industrially produced by Montedipe (Montedison, Italy).

A $^1$H-NMR spectroscopic analysis on some of these showed, for instance, that Nixolen ®NS-4 has a ratio between ethylenoxy and propylenoxy groups of 1.0/1.0, in Nixolen ®SL-8 this ratio is 1.4/1.0, in Nixolen ®VS-13 is 3.0/1.0 and in Nixolen ®VS-2600.

Different reagents, containing different Nixolen ® and/or PEGs, bases and peroxides were prepared and their activity on commercial mixtures of PCBs (Ascarel) was compared in a reaction carried out in similar conditions.

Some of these reagents are hereinafter reported.

The weight percentage of the component in the final formulation is shown between brackets.

| | | | |
|---|---|---|---|
| A | Nixolen VS-13 (86%) | $Na_2O_2$ (2%) | $K_2CO_3$ (12%) |
| B | Nixolen VS-13 (78%) | $BaO_2$ (5%) + $H_2O$ (5%) | $K_2CO_3$ (12%) |
| C | Nixolen VS-13 (86%) | $Na_2O_2$ (2%) | $CH_3ONa$ (12%) |
| D | Nixolen VS-13 (86%) | $Na_2O_2$ (2%) | $Na_2CO_3$ (12%) |
| E | Nixolen SL-8 (86%) | $Na_2O_2$ (2%) | $K_2CO_3$ (12%) |
| F | Nixolen SL-8 (83%) | $BaO_2$ (5%) | $K_2CO_3$ (12%) |
| G | Nixolen NS-4 (86%) | $Na_2O_2$ (2%) | $K_2CO_3$ (12%) |
| H | PEG 6000 (76%) + Nixolen VS-2600 (01%) | $Na_2O_2$ (2%) | $K_2CO_3$ (12%) |
| I | Nixolen VS-2600 (63%) + diethylenglycol (20%) | $Na_2O_2$ (2%) | $K_2CO_3$ (12%) |
| L | Nixolen VS-2600 (92%) | $Na_2O_2$ (2%) | Potassium t-butylate (6%) |

The reagents C and L were easily prepared at room temperature by simply mixing the components; the other reagents were prepared by stirring during 10 minutes at 85° C. in order to dissolve the base and to melt the polyethylenglycol; all the reagents are homogeneous and give a clear solution. The dehalogenating activity of the so prepared reagents on the polychlorobiphenyls, was determined by mixing 2.0 g of the reagent and 55 mg of PCBs in a thermostatic flask at 85° C.; the solution was then stirred for 3 hours, and the residual amount of PCBs was thereafter analyzed by gas-chromatographic route (HP 5880 gas chromatograph) after that the polyglycols have been removed (Florisil column, acetone as eluent).

The results are hereinafter reported; the percentage of decomposed PCBs is reported beside the letter of the used reagent: A (98%); B (76%); C (100%); D (97%); E (85%); F (59%); G (88%); I (99,8%); L (with stirring) (91%); L (without stirring) (87%).

EXAMPLE 7

Application of the reagents of the Example 6 for the decontamination of oils used in electrical power transformers and of surfaces polluted with PCBs 2.0 g of the reagent A of the Example 6 were reacted with 4 ml of Isovoltine ® oil polluted with 2%b.w. (20,000 ppm) of PCBs, stirring the biphasic mixture for three hours at 85° C.; the gas-chromatographic analysis of the treated oil showed a 97% decrease of its PCBs content; after 5 hours the reaction was over (100% decrease).

By following the same method, but using a reagent prepared from PEG 6000 (80%)+$Na_2O_2$ (8%)+ potassium t-butylate (12%), a 95% decrease after 2 hours occurred. By using tetraethylenglycol instead of PEG 6000 the observed reduction was 87%.

It should be noted that small differences in the high PCBs destruction degrees are more significant than they may appear because the residual PCBs, which are the less chlorinated, are just the less reactive.

In order to decontaminate PCBs polluted surfaces, variable quantities of these, diluted in n-hexane, were placed on a smooth glass surface and the n-hexane was allowed to evaporate. On the surfaces covered with PCBs (about 1 cm$^2$) different reagents were applied so as to cover contaminated part; the thickness of the reagent was about 1 mm.

The reagent prepared from Nixolen VS-13 (55%)+NaO$_2$ (5%)+K$_2$CO$_3$(40%) applied on 0.77 mg of PCBs showed that these reacted for 80% after 5 days at 20° C. In the same conditions, but starting from 6.4 mg of PCBs, the observed reaction was 72%.

The reagent A of Example 6, placed on 0.85 mg of PCBs gave a 67% reaction after 2 days at 20° C.

The reagent prepared from PEG 6000 (44.5%)+diethylenglycol monobutylether (44.5%)+Na$_2$O$_2$ (4.4%)+potassium t-butylate (6.6%) gave an 80% reaction after 5 days at 20° C.

The reagent prepared from Nixolen VS-2600 (83%)+Na$_2$O$_2$ (5%)+K$_2$CO$_3$ (12%), applied on 0.85 mg of PCBs gave a 70% reaction after 2 days at 20° C.

The reagent prepared from PEG 6000 (43%)+Nixolen VS-13 (43%)+Na$_2$O$_2$ (2%)+K$_2$CO$_3$ (12%), applied on 0.2 mg of PCBs, showed a 58% reaction after one day at 20° C.

EXAMPLE 8

Method of the microwaves use to favour the reaction between different reagents and various chlorinated pollutants 80 mg of PCBs were added to 2.0 g of reagent, instantly prepared at room temperature from Nixolen VS-13 (93%)+Na$_2$O$_2$ (2%)+K$_2$CO$_3$ (5%); after a normal stirring for a little while the mixture was put in a microwaves oven (Litton, 2.5 MHz) without stirring for 3 minutes the temperature, measured after said period, was 120° C. The gas-chromatographic analysis showed that 94% of PCBs were decomposed. In the same conditions, but operating with CH$_3$ONa instead of K$_2$CO$_3$, the observed reaction was 99%. In the same conditions (methylate instead of carbonate), but at 85° C. (instead of 120° C., the % of decomposed PCBs was 91%) always after 3 minutes reaction.

2.0 g of the previously described reagent in this example (sodium methylate instead of potassium carbonate) and containing 0.2 mg of 2,3,7,8-tetrachlorodibenzo-p-dioxine(dioxin) were placed for 3 minutes in a microwaves oven; the final temperature of the mixture was 120° C. The GC-MS analysis indicated that 98% of the dioxin has been decomposed.

The same reagent used for the dioxin was applied on a gres tile (porous material) having dimensions 7.5×15 cm, from which the imbued water was previously removed (treatment in the microwaves oven for 6 min. at 120° C.) and on which 0.15 g of PCBs were deposited; the tile was then placed for 3 minutes in the microwaves oven at 120° C. After cooling, it was crushed and extracted for 12 hours with acetone in Soxlhet extractor.

The gas-chromatographic analysis of the extract showed the presence of 24 mg of residual PCBs, equivalent to an 84% reaction.

What is claimed is:

1. A method for the decomposition of an halogenated organic compound which comprises reacting said compound with a reagent which consists of: component (a) at least one member selected from the group consisting of polyethyleneglycols, Nixolens ®, alcohols, polyhydroxy compounds, said polyethyleneglycols and alcohols having the formula

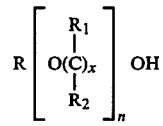

wherein:

X is 2;

n is zero or an integer from 2 to 400;

R is a linear or branched C$_1$-C$_4$ alkyl when n=0; or is hydrogen, linear or branched C$_1$-C$_{20}$ alkyl, aryl, aralkyl or acyl when n—2–400; R$_1$ and R$_2$, which are the same or different, are hydrogen, linear or branched C$_1$-C$_4$ alkyl, C$_5$-C$_8$ cycloalkyl unsubstituted or substituted, unsubstituted or substituted aryl;

Nixolens ® being liquid compounds obtained from the condensation between propylene oxide and ethylene oxide, said polyhydroxy compound having the general formula

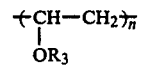

wherein n is a number between 100 and 10,000 R$_3$ is hydrogen linear or branched C$_1$-C$_6$ alkyl; component (b) a weak base, or, when Nixolen ® are used, alkali or alkaline earth metal alkoxides; component (c) an oxidizing agent or a source of free radicals.

2. The method according to claim 1, wherein said weak base component (b) is an alkali or an alkaline earth carbonate or bicarbonate.

3. The method according to claim 1, wherein said component (c) which is an oxidizing agent or said source of free radicals is an alkali or alkaline earth metal peroxide or superoxide, a persalt of an alkali or alkaline earth metal or ammonium, a salt of metal in a high valence state, alkylperoxide, alkylhydroperoxide, acylperoxide or azoisobutyronitrile.

4. The method according to claim 1, wherein said component (a) is a polyethyleneglycol of the formula H(OCH$_2$CH$_2$)$_n$OH, or an alkylether thereof, wherein n is as defined in claim 1.

5. The method according to claim 1 wherein component (a) comprises water soluble Nixolens ®.

6. The method according to claim 5, characterized in that an alkali or alkali-earth metal alkoxide is used, in the absence of the oxidizing agent.

7. The method according to claim 1 wherein said halogenated organic compound is a chlorinated organic compound and the stoichiometric ratio between said base and chlorine is greater or equal to 1 and the stoichiometric ratio between said oxidizing agent and chlorine is greater or equal to 0.5.

8. The method according to claim 1 wherein said halogenated organic compound is at least one member selected from the group consisting of polychlorodibenzodioxins, polychlorodibenzofurans, polychlorobiphenyls, polychlorobenzenes, polychlorophenols, hexachlorocyclohexane, dichlorodiphenyltrichloroethane, decachloro octahydro-1,3,4-metheno-2H-cyclobutapentalen-2-one, and their brominated and fluorinated analogs.

9. The method according to claim 1 wherein the reaction is carried out at room temperature, in the absence of air or oxygen and in the presence or in the absence of solvents miscible or immiscible with said reagent.

10. The method for the decontamination and the recovery of industrial oil contaminated from an industrial process in its original physico-chemical properties, wherein said industrial oil is reacted at room temperature and in the absence of oxygen or air with the reagent according to claim 1.

11. The method according to claim 10, wherein the reaction is carried out continuously and the industrial oil is maintained under stirring by ultrasonic treatment.

12. The method for the decontamination of soil and surfaces contaminated by at least one polyhalogenated organic compound, characterized in that said soil or surface is covered with a layer of a reagent according to claim 1 and that a viscous or solid reagent is used for non porous surfaces and a liquid reagent is used for porous surfaces and a solid film is formed over said soil or surface and said solid film is removed.

13. The method according to claim 12 characterized in that the process is carried out in the presence of electric fields, ultrasounds, infrared laser, microwaves.

14. The method according to claim 12 characterized in that the process is carried out in the presence of microwaves and that the polluted surfaces are previously treated with microwaves.

* * * * *